United States Patent
Tsuneki et al.

(10) Patent No.: US 6,169,207 B1
(45) Date of Patent: *Jan. 2, 2001

(54) PROCESS FOR PRODUCING DIALKANOLAMINES

(75) Inventors: Hideaki Tsuneki, Tokyo; Atusi Moriya, Himeji; Hideyuki Baba, Osaka, all of (JP)

(73) Assignee: Nippon Shokubai Co Ltd, Osaka (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 09/266,785

(22) Filed: Mar. 12, 1999

(30) Foreign Application Priority Data

Mar. 13, 1998 (JP) .................................. 10-063131

(51) Int. Cl.$^7$ .................................. C07C 85/18
(52) U.S. Cl. .................................. 564/475; 564/477
(58) Field of Search .................................. 564/475, 477

(56) References Cited

U.S. PATENT DOCUMENTS

| | | |
|---|---|---|
| 3,697,598 | 10/1972 | Weibull et al. . |
| 4,438,281 | * 3/1984 | Johnson, Jr. .................... 564/477 |
| 4,939,301 | 7/1990 | Grice et al. . |
| 5,599,999 | 2/1997 | Moriya et al. . |
| 5,633,408 | * 5/1997 | Watanabe et al. .................... 564/475 |

FOREIGN PATENT DOCUMENTS

| | | |
|---|---|---|
| 298636 | 3/1992 | (DE) . |
| 0652207 | 5/1995 | (EP) . |
| 49-47728 | 12/1974 | (JP) . |
| 2225446 | 9/1990 | (JP) . |
| 173114 | 7/1995 | (JP) . |
| 158167 | 3/1957 | (SE) . |

OTHER PUBLICATIONS

Chemical Abstracts, vol. 099, No. 22, Nov. 28, 1983, Columbus, Ohio, US; abstract No. 182217.

Chemical Abstracts, vol. 105, No. 13, Sep. 29, 1986, Columbus, Ohio, US; abstract No. 114424.

Chemical Abstracts, vol. 083, No. 1, Jul. 7, 1975, Columbus, Ohio, US; abstract No. 008664.

Chemical Abstracts, vol. 104, No. 14, Apr. 7, 1986, Columbus, Ohio, US; abstract No. 111765.

Chemical Abstracts, vol. 094, No. 17, Apr. 27, 1981, Columbus, Ohio, US; abstract No. 139137.

Industrial and Engineering Chemistry, Product Research and Development, (1986), 25:424–430.

"Ion–Exchange–Introduction on Theory and Practice", (1981), Maruzen Co., Tld., p. 34.

* cited by examiner

Primary Examiner—Samuel Barts (57) ABSTRACT

The invention provides a process for producing dialkanolamines through amination of alkylene oxide with ammonia at liquid phase, in which side formation of trialkanolamines is inhibited and dialkanolamines can be produced with high selectivity and high efficiency. Said process is carried out in the presence of a catalyst which possesses such reaction characteristics that render the rate constant $\alpha$ of the reaction between ammonia and alkylene oxide not less than 0.10, when the reaction rate constant between monoalkanolamine and alkylene oxide is 1, and the rate constant $\beta$ of the reaction between dialkanolamine and alkylene oxide not more than 0.7, when the reaction rate constant between monoalkanolamine and alkylene oxide is 1.

28 Claims, 2 Drawing Sheets

FIG. 1

NH₃/EO molar Ratio

EO: ethylene oxide
MEA: monoethanolamine
DEA: diethanolamine
TEA: triethanolamine

FIG. 2

MEA: monoethanolamine
DEA: diethanolamine
TEA: triethanolamine

PROCESS FOR PRODUCING DIALKANOLAMINES

This invention relates to a process for selectively producing dialkanolamines, through amination of alkylene oxides with ammonia.

As a method of producing alkanolamines through amination of alkylene oxides with ammonia, industrial production of ethanolamines through the reaction of ethylene oxide with aqueous ammonia (ammonia concentration=20–40 percent by weight) is being practiced. In this method three kinds of ethanolamines, i.e., monoethanolamine, diethanolamine and triethanolamine are formed. Whereas, demand for triethanolamine is decreasing, and it is desirable to inhibit formation of triethanolamine. For this purpose, the reaction is conducted using a large excess of ammonia, such as at the molar ratio of ammonia to ethylene oxide of 3–5, but still the selectivity for triethanolamine ranges 10–20 percent by weight or even higher, and that for diethanolamine is not more than 40 percent by weight.

Whereas, alkylene oxide hardly react with ammonia in a water-free system and hence presence of a catalyst is essential for this type of reaction. As the catalyst, for example, those of a homogeneous system such as of organic acids, inorganic acids or ammonium salts have been proposed (cf. Swedish Patent No. 158167). Those homogeneous system catalysts, however, have the problem that their separation from the reaction system is difficult, and their performance is insufficient.

As an attempt to immobilize these homogeneous system acid catalysts, an ion-exchange resin formed by immobilizing sulfonic acid groups on the resin has been proposed (cf. JP KOKOKU Sho 49(1974)-47728). This catalyst exhibits relatively high activity and selectivity, and is being put to industrial practice. The ion-exchange resin, however, is subject to a problem that its usable maximum temperature is low. The highest allowable temperature of use of ordinary commercial ion-exchange resins is in the order of around 120° C., i.e., considerably low [(see *ION KOKAN—RIRON TO ŌYŌ ENO TEBIKI* (ion-exchange—handbook of theory and application—)], co-translated by Rokuro Kuroda and Masami Shibukawa, 1981, Maruzen Kabushiki Kaisha, p. 34). Hence when the reaction is conducted at a low molar ratio of ammonia to ethylene oxide, the reaction heat causes the temperature rise in the catalyst bed beyond the allowable maximum level, and a prolonged use of the catalyst under such temperature condition invites its deterioration. For this reason, it is difficult to lower the ammonia/ethylene oxide molar ratio to about 20–25 or less.

With the view to overcome the defect in ion-exchange resins that their heat resistance is low, inorganic catalyst excelling in heat stability has been investigated. U.S. Pat. No. 4,438,281 disclosed that generally frequently used silica-alumina exhibited the activity. *Industrial & Engineering Chemistry, Product Research & Development*, 1986, Vol. 25, pp. 424–430 gave a comparative study of ion-exchange resins, various zeolite catalysts and the like, according to which the studied inorganic catalysts did not show better selectivity for monoalkanolamines than that of the ion-exchange resins. Japan KOKAI Hei 2(1990)-225446 disclosed acid-activated clay catalysts, some of which gave monoethanolamine yield as high as 60 percent by weight or even higher. Their selectivity for monoalkanolamines, however, is insufficient and hence the reactions using those catalysts are conducted at ammonia/ethylene oxide molar ratio of 20–30 or still higher, which necessitates high equipment costs for recovery and recirculating use of ammonia and gives rise to many practical difficulties.

As a solution to these problems, Japan KOKAI Hei 7(1995)-173114 proposes as high activity catalysts capable of producing monoalkanolamine with high selectivity, rare earth elements supported on heat-resistant carriers. The object of these catalysts, however, lies in monoalkanolamine production with high selectivity and their performance for producing dialkanolamine while inhibiting side-production of trialkanolamine is still unsatisfactory. Moreover, when such a catalyst exhibiting high selectivity for monoalkanolamine is used, dialkanolamine yield can be increased by recycling a part of the formed and separated monoalkanolamine into the reaction system. In actual practice, however, problems still remain such as high utility costs for the recycling.

East German Patent 298,636 has disclosed a method of selectively synthesizing dialkanolamine through a vapor-phase reaction using a sodium salt of crystalline alminosilicate as the catalyst. Whereas, diethanolamine selectivity in said method was at the most only 23 percent by weight and in that occasion as much as 22 percent by weight of triethanolamine was formed. Thus, the method cannot be regarded suitable for industrial production of diethanolamine.

This invention is made for solving the above problems. The object of the invention is to provide a method for producing dialkanolamine with high selectivity and at high efficiency while inhibiting formation of undesirable side products such as trialkanolamine, in the occasion of preparing dialkanolamine by amination of alkylene oxide with ammonia.

We have engaged in concentrative studies aiming at finding a solution to the above problems, to find that a catalyst having a specific rate constant of reaction is advantageous for the dialkanolamine production. The present invention is thus completed.

Namely, the production method according to the present invention is characterized by, in an occasion of producing a dialkanolamine which is expressed by the general formula (II) below:

(wherein $R^1$, $R^2$, $R^3$, $R^4$, $R^5$, $R^6$, $R^7$ and $R^8$ each independently stands for a hydrogen atom, methyl group or ethyl group)

through a reaction of an alkylene oxide represented by the general formula (I) below:

(I)

(wherein $R^1$, $R^2$, $R^3$ and $R^4$ each independently stands for a hydrogen atom, methyl group or ethyl group)
with ammonia at liquid phase, in the presence of a catalyst, carrying out said reaction under the conditions such that (i) the rate constant $\alpha$ of the reaction between ammonia and alkylene oxide of at least 0.10, when the rate constant between monoalkanolamine and alkylene oxide is 1, and (ii) the rate constant $\beta$ of the reaction between dialkanolamine and alkylene oxide of not more than 0.7, when the rate constant between monoalkanolamine and alkylene oxide is 1.

Mole number of said ammonia is preferably in the range of not less than $2\beta/\alpha^{0.3}$ and not more than $1/(1.5\alpha\beta^{0.5})$, per mole of the alkylene oxide.

Preferred catalyst has an $\alpha$ between 0.10 to 1, in particular, between 0.10 and 0.5; and a $\beta$ not more than 0.7, in particular, not more than 0.5, inter alia, not more than 0.25.

The catalyst preferably is a microporous material having an effective pore size ranging from 0.45 nm to 0.8 nm.

The catalyst preferably is a metallosilicate which has been ion-exchanged with a rare earth element.

The catalyst preferably has the outer surfaces of its primary particles which have been given an deactivating treatment.

The invention shall be explained in further details hereinafter.

The reaction of ammonia with an alkylene oxide is a sequential reaction, and for selectively producing dialkanolamine, which is an intermediate product, use of a catalyst excelling in selectivity is required. Namely, in said reaction, for example, the following three reactions sequentially take place:

(1)

(2)

(3)

Presuming that the reactions (1), (2) and (3) are primary in regard to the respective concentration of the starting materials, alkylene oxide and ammonia and the amines and when the rate constants of the reaction formulae are $k_1$, $k_2$ and $k_3$, respectively, the respective reaction rate can be expressed as follows:

$$r_1 = k_1 C_{NH_3} C_{AO} \quad (4)$$

$$r_2 = k_2 C_{MAA} C_{AO} \quad (5)$$

$$r_3 = k_3 C_{DAA} C_{AO}. \quad (6)$$

Here the $\alpha$ and $\beta$ are defined as follows:

$$\alpha = k_1/k_2$$

$$\beta = k_3/k_2.$$

When mole fractions of $NH_3$, MAA, DAA and TAA in the reaction liquid where the AO conversion is 100% are expressed as x, y, z and u, respectively, $\alpha$ and $\beta$ are the solutions of the following nonlinear equations (i) and (ii), respectively, based on the integration of the equations of reaction rate (4)–(6) and the equation of material balance (x+y+z+u=1). These nonlinear equations can be solved by ordinary method of numerical solution, to give the values of $\alpha$ and $\beta$:

$$y = \frac{x^{1/\alpha} - x}{1 - 1/\alpha} \quad (i)$$

$$z = \frac{\alpha}{\alpha - 1}\left(\frac{x - x^{\beta/\alpha}}{\alpha - \beta} - \frac{x^{1/\alpha} - x^{\beta/\alpha}}{1 - \beta}\right) \quad (ii)$$

In consequence of the investigations in the reaction for producing dialkanolamine from alkylene oxide and ammonia at liquid phase in the presence of a catalyst, we have discovered that dialkanolamine can be selectively produced with high efficiency, by carrying out the reaction under the conditions such that (i) said $\alpha$ is at least 0.10; preferably in the range of 0.10 to 1; in particular, in the range of 0.10 to 0.5; inter alia, in the range of 0.10 to 0.30: and (ii) said $\beta$ is not more than 0.7; preferably not more than 0.5; in particular, not more than 0.4; inter alia, not more than 0.25.

When the value of $\alpha$ is less than the above lower limit of 0.10, the molar ratio of ammonia to starting alkylene oxide in the production of monoalkanolamine which is the first reaction product must be made high, which lowers the efficiency. Conversely, when it is more than the upper limit of the specified range, alkylene oxide concentration becomes excessively high to necessitate removal of heat from the reaction system, while the molar ratio of ammonia to the alkylene oxide can be reduced.

Again, when $\beta$ exceeds the above-specified upper limit, the sequential reaction from dialkanolamine to trialkanolamine becomes vigorous, rendering the selective production of dialkanolamine impossible. It follows that a catalyst whose $\beta$ value is zero may be used to entirely inhibit formation of trialkanolamine. Whereas, differently from the reaction between ammonia and alkylene oxide, the one between alkanolamine and alkylene oxide progresses to a certain extent even in the absence of catalyst, and hence a catalyst of $\beta$=0 theoretically cannot exist. Thus $\beta$ needs to be more than zero and not more than 0.7.

We have furthermore discovered that the selectivity for dialkanolamine can be still improved by suitably controlling the molar ratio between the starting materials within an appropriate range. That is, we have discovered that use of the starting reactants of the composition wherein the starting mole number of the ammonia is in the range of between $2\beta/\alpha^{0.3}$ and $1/(1.5\alpha\beta^{0.5})$ per mole of alkylene oxide is preferred for the selective production of dialkanolamine.

For example, when $\alpha=0.167$ and $\beta=0.25$, the lower limit of the molar ratio is calculated to be $2\times0.25/0.167^{0.3}=0.856$; and the upper limit, $1/(1.5\times0.167\times0.25^{0.5})=8.0$. Changes in product distribution corresponding to variation in the molar ratio within the above-specified range is schematically shown as to a case wherein alkylene oxide is ethylene oxide, in appended FIG. 1.

In the FIGS. 1 and 2.

EO signifies ethylene oxide,
MEA signifies monoethanolamine,
DEA signifies diethanolamine, and
TEA signifies triethanolamine.

Figure 1:
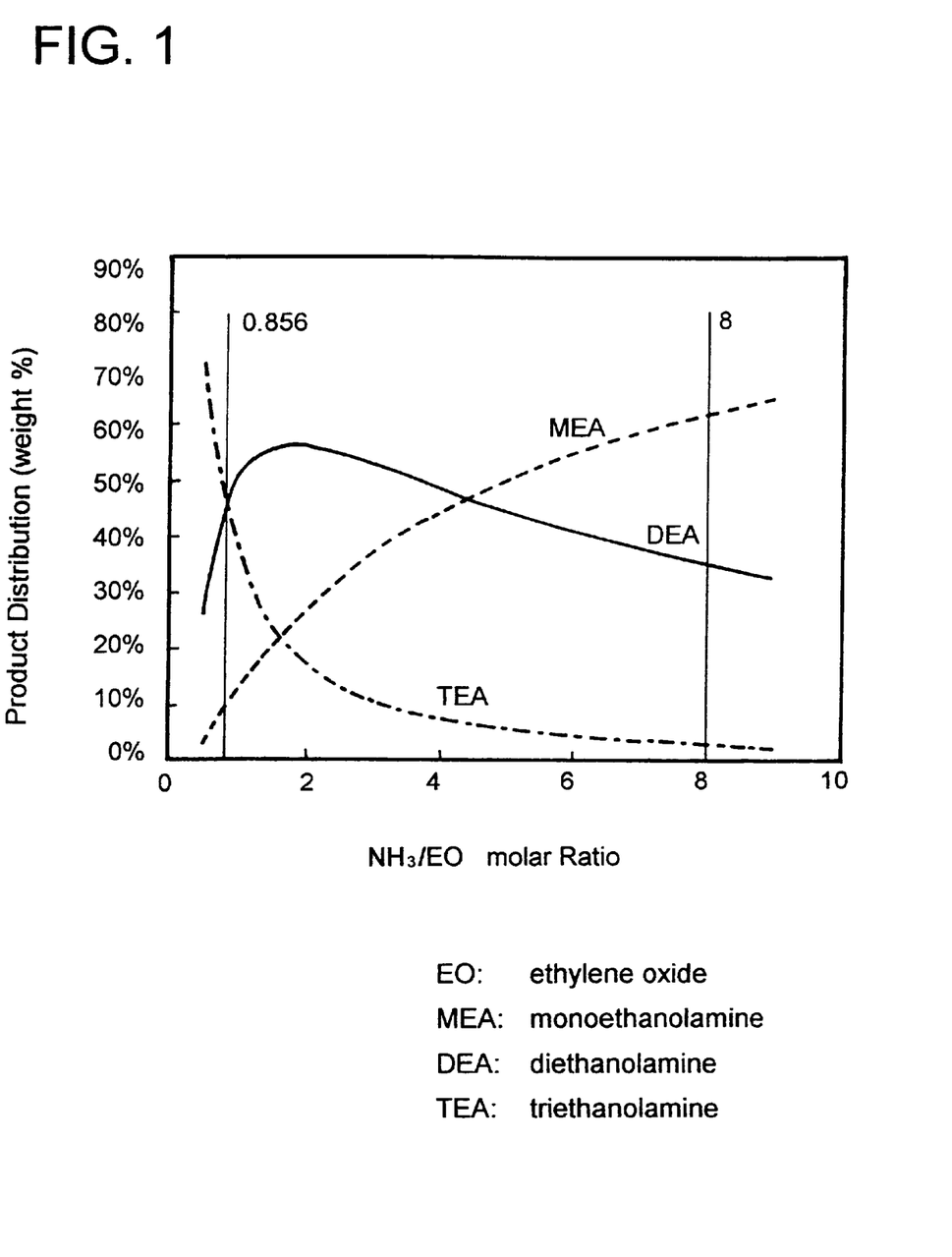
FIG. 1 among the appended drawings is a graph showing distribution of ethanolamines in the product formed in the reaction of starting ammonia with ethylene oxide with the molar ratio between the starting materials varied. The molar ratio (mole number of ammonia to ethylene oxide) is taken on the horizontal axis and the formation ratios among (mono-, di- and tri-) ethanolamines (percent by weight), on the vertical axis.

When the molar ratio is less than the lower limit of 0.856 in this model, diethanolamine (DEA) decreases and triethanolamine (TEA) notably increases. Whereas, when it exceeds the upper limit of 8.0, triethanolamine (TEA) yield is low, but that of diethanolamine (DEA) also is low. Hence, the molar ratio preferably lies within the said range, when selective formation of diethanolamine (DEA) is intended.

The catalysts according to the invention are those which are suitably used for the reaction to produce dialkanolamine at liquid phase, from alkylene oxide and ammonia. So long as they exhibit such reaction characteristics that aforesaid $\alpha$ is at least 0.10, preferably in the range of 0.10 to 1, in particular, between 0.10 and 0.5, inter alia, between 0.10 and 0.30; and $\beta$ is not more than 0.7, preferably not more than 0.5, in particular, not more than 0.4, inter alia, not more than 0.25, they are subject to no further limitation. While preparation method of the catalyst is not critical, it is recommendable to optimize, for example, acidity, basicity, pore structure and crystal structure, etc. of the catalyst in the course of preparation. More specifically, such a method as utilizing shape selectivity of a microporous material, e.g., zeolite. In the above method microporous materials refer to crystal substances having molecular order of pores of uniform diameter, which include metallosilicate type and aluminophosphate type.

As metallosilicate type material aluminosilicate whose metal component is aluminum is well known by the name of zeolite. As metals to form other metallosilicates, Fe, Ga, B, Co, Ni, Cr, Sc, Ge and Ti, etc. are known.

As aluminophosphate type, aluminophosphate (ALPO), metalloaluminophosphate (MAPO) and silicoaluminophosphate (SAPO) are known.

The reaction between alkylene oxide with ammonia or amine takes place mainly within the pores, and therefore effective micropore diameter of above-described microporous crystal is within a range of 0.45–0.8 nm, preferably, 0.5–0.7 nm, for the crystal to exhibit selectivity. Examples of such microporous crystal include ZSM-5, ZSM-11, ALPO-31, SAPO-40 and BETA.

Above-specified range of effective micropore diameter is preferred because it does not hinder diffusion of the starting materials into the pores to decrease the activity and, conversely, prevents formation of trialkanolamines in the pores so that the selectivity for dialkanolamines does not drop.

X-type or Y-type zeolite having large cavities inside allow formation of large molecules in the cavities and hence seldom exhibit the shape selectivity expected of the pore diameters at the entrances and exits of the pores.

Again, shape selectivity cannot be expected for the reaction outside the pores and, therefore it is preferred to deactivate outer surfaces of primary particles of the crystals. Means of such deactivation treatment comprise high-temperature steaming, silicon tetrachloride treatment and alkoxysilane treatment. In synthesis of microporous material, alkali metal ions are present at the ion-exchange sites. In that condition, the material has little acidity and exhibits low activity. It is therefore preferred to exchange the alkali metal ions with proton, ammonium ion, polyvalent cation (rare earth elements are particularly preferred) and the like to raise the activity level.

As a concrete production method of microporous material, metallosilicate can normally be prepared by dispersing a silica source, metal source and structural directing agent in water and heating the dispersion in an autoclave, i.e., by a so-called hydrothermal synthesis method. ALPO, MAPO and SAPO can similarly be prepared by hydrothermal synthesis, except that phosphoric acid is used. ZSM-5 and BETA are commercially available, which may be used in their marketed form. Those hydrothermally synthesized microporous materials normally contain alkali metals as pair cations and, therefore, they can be converted to proton-type by once ion-exchanging with $NH_3$ ions and then sintering at high temperatures. It is also possible to ion-exchange with polyvalent cations. In particular, when exchanged with a rare earth element, the material frequently exhibits improvement in both the catalytic activity and selectivity, and therefore is preferred.

For industrial utilization, the catalysts needs to be shaped. Metallosilicate consists of extremely fine crystals and exhibits very poor shaping property by itself. Therefore, in many cases an promoter or binder has to be used for its shaping. As useful promoter or binder, various oxide sols such as silica sol, alumina sol, zirconia sol and the like or clay minerals are used. From the standpoint of improving the shapability, clay minerals such as smectite-type and kaolin are preferred. For not imparing the activity and selectivity inherent in individual catalyst, smectite-type clays which themselves are active in the ammonia-alkylene oxide reaction, in particular, montmorillonite, are preferred. Furthermore, montmorillonite which has been ion-exchanged with polyvalent metal cations, in particular, a rare earth element, is preferred. When such a shaping promoter is used, shaping progresses smoothly, and because that shaping promoter itself possesses activity selectivity, it does not impair the inherent performance of the catalyst of the present invention. It is also preferred to increase the pore volume, to prevent deterioration of the activity and selectivity of the catalyst which has been shaped to be given a significant volume under the influence of diffusion inside said catalyst. This can be accomplished by adding a pore-forming agent during the shaping and removing it through the calcinating operation to increase the pore volume. As the pore-forming agent, various ammonium salts such as ammonium nitrate or ammonium acetate, organic compounds such as oxalic acid, urea, and the like and water-insoluble organic compounds such as polymers and fibers may be named. From the standpoint of pore-forming efficiency and ease of shaping, water-insoluble organic compounds can be conveniently used. As the water-insoluble organic compounds, those having a significant level of hygroscopicity, being in fine powder form and removable by burning by a high temperature treatment in the order of several hundred degrees Celsius are useful. In particular, crystalline cellulose is preferred because of ease of handling. As crystalline cellulose, powder formed by grinding filter paper or pulverizing pulp are used. When an organic pore-forming agent such as crystalline cellulose is used, a simple heating treatment cannot decompose and remove it, and hence it is burnt and removed in an oxygen-containing gas. Air is conveniently used for this purpose.

One of the starting materials in the present invention, alkylene oxides, are those expressed by the earlier given general formula (I), examples of which including those containing 2 to 4 carbon atoms such as ethylene oxide, propylene oxide, and the like. In correspondence to these starting materials, alkanolamines of said general formula (II) are obtained. As specific examples, monoethanolamine, diethanolamine, triethanolamine, propanolamine and the like may be named.

The reaction must be carried out at liquid phase, and hence it is generally necessary to maintain the reaction pressure at a level higher than the vapor pressure of the reaction liquid at the highest temperature inside the reactor. Whereas, when the alkylene oxide concentration is excessively high to render removal of the reaction heat difficult, it is also possible to vaporize a part of the ammonia and remove the reaction heat with its latent heat of vaporization. In that case, it is preferred to maintain the reaction pressure at a level lower than the vapor pressure of the reaction liquid at the highest temperature inside the reaction system.

Normally, production of alkanolamines can be carried out at temperatures in the range of 40–300° C. The preferred range is 80–200° C. Suitable operation pressure ranges 1–20 MPa.

Under the above-described conditions, the liquid's hourly space velocity (LHSV) is subject to no critical limitation, while normally that of at least 1 hr$^{-1}$ is used.

When the process of this invention is adopted, it is possible to produce dialkanolamine at a high efficiency, without recycling the formed monoalkanolamine. Whereas, it is also possible to increase the dialkanolamine yield by recycling a part of the formed monoalkanolamine into the reactor, when alkylene oxide concentration at the entrance into the reactor is subject to restrictions, eg., in case the process is practiced by an adiabatic single stage reaction, or when a large quantity monoalkanolamine production is unnecessary.

The amount to be recycled varies depending on the desired production amount of monoalkanolamine and the ammonia/alkylene oxide molar ratio in the starting material. Taking an example in diethanolamine production, preferably the quantity of monoethanolamine to be recycled, to the total ethanolamine quantity produced, is not more than $0.3R\beta^{0.5}$ by weight, when R represents the mole number of ammonia per mole of ethylene oxide at the entrance into the reactor. When the recycled amount is more than the said limit, utility costs for the recycling notably increases or unnecessarily large size reactor is needed, which is undesirable.

Figure 2:
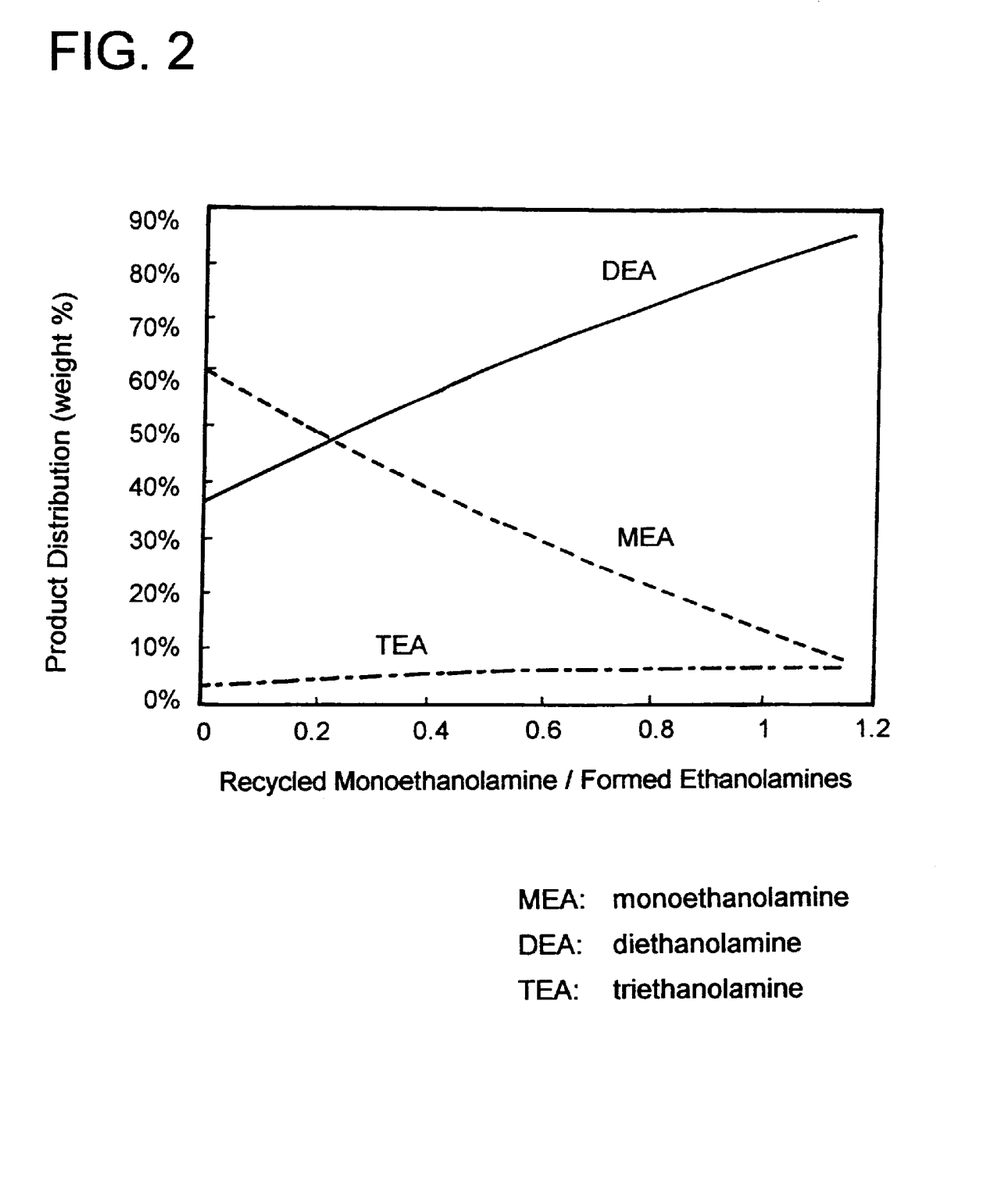
FIG. 2 is a graph showing distribution of ethanolamines formed in the reaction of ammonia with ethylene oxide at a starting molar ratio of 8, in the products formed with the amount of recycled monoethanolamine varied. The weight ratio of the recycled monoethanolamine to the formed ethanolamine is taken on the horizontal axis and the formation ratio of (mono-, di-, and tri-) ethanolamines (weight %), on the vertical axis.

FIG. 2 shows variation in the product distribution corresponding to the change in recycled amount of monoethanolamine under $\alpha=0.167$ and $\beta=0.25$, according to which $0.3R\beta^{0.5}=1.2$ is the approximate upper limit of the recycling at which about 90% by weight of diethanolamine can be obtained, however with increased utility costs.

In the following Examples, production examples of mainly ethanolamines from ethylene oxide and ammonia are given, which are intended for explanation only and should never be construed to limit the scope of the present invention.

In the Examples, the terms LHSV, ethylene oxide conversion and diethanolamine selectivity are used with the following definitions. Furthermore, the formed reaction mixture contains nearly no product other than ethanolamines, and hence the ethylene oxide conversion (mole %) is approximately the same to the total yield (mole %) of (mono, di and tri) ethanolamines based on the starting ethylene oxide.

$$LHSV = \frac{[\text{volume of liquid starting material (cm}^3\text{/hr) passing through reactor per hour}]}{[\text{volume (cm}^3\text{) of catalyst in the reactor}]}$$

Ethylene oxide conversion =

$$\frac{[\text{mole number of ethylene oxide consumed for the reaction}]}{[\text{mole number of ethylene oxide supplied to the reactor}]} \times 100 \text{ (mole \%)}$$

Diethanolamine selectivity =

$$\frac{[\text{weight of diethanolamine in product}]}{[\text{weight of total ethanolamines in the product}]} \times 100 \text{ (weight \%)}.$$

REFERENTIAL EXAMPLE 1

A pentasil-type aluminosilicate (crystal structure=MFI form, Al/Si atomic ratio=1/30, specific surface area=380 m$^2$/g, pore size=0.54×0.56 nm) was given a hydrochloric acid treatment and whereby ion-exchanged with proton. Then the outer surface of the crystals was treated with tetramethoxysilane and deactivated. The treating conditions were 15 hours' treatment at 400° C. in helium gas stream. Next, after an hour's treatment in tetramethoxysilanesaturated helium gas stream at 70° C., the crystals were degasified at 400° C. in helium gas stream for 3 hours. This degasification treatment was repeated 4 times, followed by 5 hours' treatment with steam-saturated helium at 200° C. and finally calcined in air at 400° C. for an hour. The product was used as catalyst A.

REFERENTIAL EXAMPLE 2

Ten (10) grams of the catalyst A was added to 100 cm$^3$ of 1 mole/dm$^3$ aqueous lanthanum nitrate solution under stirring. Stirring was continued for a day at room temperature, followed by filtration. The residual solid was washed with 500 cm$^3$ of pure water. The resulting cake was dried for a day at 100° C., and pulverized to particle sizes of 0.1–0.2 mm to be used as the catalyst. This is referred to as catalyst B.

REFERENTIAL EXAMPLE 3

A pentasil-type iron silicate (crystal structure=MFI form, Fe/Si atomic ratio=1/25, specific surface area=350 m$^2$/g, pore size=0.54×0.56 nm) was ion-exchanged with proton, and outer surfaces of the crystals were given an deactivation treatment through the sequence of procedures same to those practiced in Referential Example 1. This is referred to as catalyst C.

EXAMPLE 1

Stainless steel tube reactors (5 mm in inner diameter) of each 3 cm$^3$ in capacity were filled with the catalyst A which was obtained in Referential Example 1. Ammonia and ethylene oxide were fed into the reactors at a fixed rate with a high pressure pump, and the reactors were heated in an oil bath. The reaction pressure was maintained at 14 MPa. Each reaction liquid was collected and analyzed with gas chromatography. The reaction conditions and the results were as indicated in Table 1.

EXAMPLES 2–3

Example 1 was repeated except that the catalyst A was replaced with the catalysts B and C which were obtained in Referential Examples 2 and 3, respectively. The reaction conditions and the results of the analysis were as indicated in Table 1.

EXAMPLE 4

For the purpose of confirming the effect of recycling of monoethanolamine in Example 2, monoethanolamine was added to the starting material and the reaction of Example 2 was conducted, under the reaction conditions of: composition of the starting material, ammonia/monoethanolamine/ethylene oxide (molar ratio)=8/0.7/1; LHSV=12 hr$^{-1}$; and oil bath temperature=100° C.

The product distribution at the exit of the reactor in this Example was: monoethanolamine 51.7 wt %, diethanolamine 44.4 wt % and triethanolamine 3.9 wt %. The monoethanolamine at the reactor exit was not recovered as a product as it was, but a part of which was recycled. The product distribution after the recycled portion was compensated was: monoethanolamine 13.0 wt %, diethanolamine 80.0 wt % and triethanolamine 7.0%. The recycling thus enabled very high diethanolamine yield.

The amount of the recycled monoethanolamine to the formed ethanolamines was 80% by weight.

COMPARATIVE EXAMPLES 1–2

To 10 dm$^3$ of a 0.05 mole/dm$^3$ aqueous solution of lanthanum nitrate, 200 g of montmorillonite was added with stirring. The stirring was continued for a day at room temperature, followed by filtration. The residual solid was washed with 10 dm$^3$ of pure water. The cake was dried for a day at 100° C., and then pulverized to a size not greater than 200 mesh. Thus a catalyst bulk was obtained.

To 100 g of this catalyst powder, an equal amount of pure water was added once again, kneaded with a kneader and dried for a day at 100° C. Then the dried catalyst was given a high temperature treatment at 500° C., for 5 hours while gassing with air. The resultant solid was pulverized to a particle size 0.1–0.2 mm, to serve as the catalyst which carried 14 wt % of lanthanum. This catalyst is referred to as catalyst X.

Example 1 was repeated except that catalyst A was replaced with this catalyst X. The reaction conditions and the results were as indicated in Table 2. This catalyst X exhibited a high α value and was found to be suitable for monoethanolamine production, but was apt to form triethanolamine because of its high β value.

COMPARATIVE EXAMPLES 3–4

Example 1 was repeated except that the catalyst A was replaced with DOWX-50W (50–100 mesh). The reaction

TABLE 1

| Example No. | Catalyst | α | β | molar ratio NH$_3$/EO | LHSV hr$^{-1}$ | Oil bath temp. ° C. | Product Distribution (wt. %) | | |
|---|---|---|---|---|---|---|---|---|---|
| | | | | | | | MEA | DEA | TEA |
| 1 | A | 0.167 | 0.35 | 5.9 | 10.5 | 110 | 54.4 | 39.7 | 5.8 |
| 2 | B | 0.125 | 0.22 | 7.9 | 11.5 | 100 | 55.2 | 41.1 | 3.7 |
| | | | | 4.0 | 8.1 | 95 | 37.7 | 53.1 | 9.2 |
| 3 | C | 0.155 | 0.21 | 4.1 | 7.0 | 95 | 43.3 | 50.0 | 6.7 |
| | | | | 7.8 | 10.5 | 100 | 59.8 | 37.5 | 2.7 |

MEA: monoethanolamine
DEA: diethanolamine
TEA: triethanolamine conditions and the results were as indicated in Table 2. It can be understood from the data in Table 2 that this catalyst exhibited poor selectivity both for monoethanolamine and diethanolamine, because its α-value was not unordinarily large but its β-value was high.

COMPARATIVE EXAMPLES 5–6

Example 1 was repeated except that the catalyst A was replaced with stabilized Y-form zeolite (abbreviated name: USY; Toso Kabushiki Kaisha, HSZ-350 HUA; pore size≈0.8 nm, having large inside cavities). The reaction conditions and the results were as indicated in Table 2. It can be understood from the given data that this catalyst tended strongly to produce triethanolamine because of its high β-value.

COMPARATIVE EXAMPLE 7

Example 1 was repeated except that the catalyst A was replaced with Molecular Sieve 3A. Because the pore size of Molecular Sieve 3A was extremely small as about 0.3 nm, it exhibited very low reaction activity and even under such conditions as the oil bath temperature of 150° C., LHSV of 2–9 hr$^{-1}$ and NH$_3$/EO molar ratio of 14.3, still the conversion did not exceed 71%.

COMPARATIVE EXAMPLE 8

Into a solution formed by dissolving 51 g of phosphorus wolframate-29-hydrate in 100 cm$^3$ of water, 10 g of 50–100 mesh silica gel was thrown, and was evaporated to dryness on a hot water bath under stirring. Thus recovered solid was dried at 120° C. for 10 hours, followed by 2 hours' sintering at 300° C. This catalyst is referred to as catalyst Y.

Example 1 was repeated except that the catalyst A was replaced with catalyst Y. The reaction conditions and the results were as indicated in Table 2. It can be understood that the monoethanolamine selectivity of this catalyst was poor even under a large excess of NH$_3$, because of its low α-value; and also because of its large β-value, it strongly tended to form triethanolamine.

alkylene oxide can be reduced compared with those in conventional methods.

Moreover, because the invention achieves equivalent production ratios of alkanolamines without recycling the formed monoalkanolamine into the reaction system, the recovery cost of unreacted ammonia can be reduced and, at the same time, the total amount of the starting supply decreases. This enables reduction in sizes of the apparatuses in the reaction system as well as the recovery system, leading to reduced plant and equipment costs. The merits of the present invention are thus very substantial.

What is claimed is:
1. A process for producing dialkanolamines which comprises reacting an alkylene oxide represented by formula (I) below:

(I)

(wherein R$^1$, R$^2$, R$^3$ and R$^4$ each independently stands for a hydrogen atom, methyl group or ethyl group)

with ammonia at liquid phase, in the presence of a catalyst, whereby producing a dialkanolamine of the following formula (II):

TABLE 2

| Comparative Example No. | Catalyst | α | β | molar ratio NH$_3$/EO | LHSV hr$^{-1}$ | Oil bath temp. ° C. | Product Distribution (wt. %) | | |
|---|---|---|---|---|---|---|---|---|---|
| | | | | | | | MEA | DEA | TEA |
| 1 | X | 0.323 | 1.06 | 10.2 | 10.3 | 95 | 79.5 | 17.8 | 2.6 |
| 2 | | | | 4.1 | 7.0 | 90 | 59.5 | 29.5 | 11.0 |
| 3 | DOW | 0.18 | 0.98 | 11.0 | 10.8 | 95 | 70.1 | 24.6 | 5.3 |
| 4 | X50W | | | 4.0 | 6.1 | 85 | 45.6 | 34.7 | 19.7 |
| 5 | USY | 0.125 | 1.44 | 15.1 | 10.9 | 130 | 69.0 | 21.9 | 9.1 |
| 6 | | | | 8.1 | 8.9 | 120 | 54.6 | 26.0 | 19.5 |
| 8 | Y | 0.0901 | 1.47 | 15.0 | 10.1 | 111 | 62.0 | 26.1 | 11.9 |

MEA: monoethanolamine
DEA: diethanolamine
TEA: triethanolamine

According to the present invention, in dialkanolamine production through amination of alkylene oxide with ammonia, side-formation of trialkanolamine can be inhibited and dialkanolamine can be produced at high selectivity and high efficiency. Because of the high selectivity for dialkanolamine formation, the molar ratio of ammonia to (wherein $R^1$, $R^2$, $R^3$, $R^4$, $R^5$, $R^6$, $R^7$ and $R^8$ each independently stands for a hydrogen atom, methyl group or ethyl group), said process being characterized in that said reaction is carried out under the conditions such that (i) the rate constant a of the reaction between ammonia and the alkylene oxide is at least 0.10, when the rate constant between the monoalkanolamine and the alkylene oxide is 1, and (ii) the rate constant $\beta$ of the reaction between the dialkanolamine and the alkylene oxide is not more than 0.7, when the rate constant between the monoalkanolamine and the alkylene oxide is 1.

2. A process for producing dialkanolamines according to claim 1, in which the catalyst is a microporous material having an effective pore size ranging from 0.45 nm to 0.8 nm.

3. A process for producing dialkanolamines according to claim 1, in which the catalyst is a metallosilicate which has been ion-exchanged with a rare earth element.

4. A process for producing dialkanolamines according to claim 1, in which the catalyst has the outer surfaces of its primary particles which have been given a deactivating treatment.

5. A process for producing dialkanolamines according to claim 1, in which said reaction rate constant $\alpha$ is in the range of 0.10 to 0.30, and said reaction rate constant $\beta$ is not more than 0.25.

6. A process for producing dialkanolamines according to claim 1, in which a part or all of the formed monoalkanolamine is recycled into the starting material system.

7. A process for producing dialkanolamines according to claim 6, in which the amount of the monoalkanolamine to be recycled into the starting material system is not more than $0.3R\beta^{0.5}$ to the amount of the total alkanolamines formed, when the mole number of ammonia per mole of the starting alkylene oxide is R.

8. A process for producing dialkanolamines according to claim 1, in which mole number of the ammonia is in the range of not less than $2\beta/\alpha^{0.3}$ and not more than $1/(1.5\alpha\beta^{0.5})$, per mole of the alkylene oxide.

9. A process for producing dialkanolamines according to claim 8, in which the catalyst is a metallosilicate which has been ion-exchanged with a rare earth element.

10. A process for producing dialkanolamines according to claim 8, in which the catalyst has the outer surfaces of its primary particles which have been given a deactivating treatment.

11. A process for producing dialkanolamines according to claim 8, in which said reaction rate constant $\alpha$ is in the range of 0.10 to 0.30, and said reaction rate constant $\beta$ is not more than 0.25.

12. A process for producing dialkanolamines according to claim 8, in which a part or all of the formed monoalkanolamine is recycled into the starting material system.

13. A process for producing dialkanolamines according to claim 12, in which the amount of the monoalkanolamine to be recycled into the starting material system is not more than $0.3R\beta^{0.5}$ to the amount of the total alkanolamines formed, when the mole number of ammonia per mole of the starting alkylene oxide is R.

14. A process for producing dialkanolamines according to claim 8, in which the catalyst is a microporous material having an effective pore size ranging from 0.45 nm to 0.8 nm.

15. A process for producing dialkanolamines according to claim 14, in which the catalyst has the outer surface of its primary particles which have been given a deactivating treatment.

16. A process for producing dialkanolamines according to claim 14, in which said reaction rate constant $\alpha$ is in the range of 0.10 to 0.30, and said reaction rate constant $\beta$ is not more than 0.25.

17. A process for producing dialkanolamines according to claim 14, in which a part or all of the formed monoalkanolamine is recycled into the starting material system.

18. A process for producing dialkanolamines according to claim 17, in which the amount of the monoalkanolamine to be recycled into the starting material system is not more than $0.3R\beta^{0.5}$ to the amount of the total alkanolamines formed, when the mole number of ammonia per mole of the starting alkylene oxide is R.

19. A process for producing dialkanolamines according to claim 14, in which the catalyst is a metallosilicate which has been ion-exchanged with a rare earth element.

20. A process for producing dialkanolamines according to claim 19, in which said reaction rate constant $\alpha$ is in the range of 0.10 to 0.30, and said reaction rate constant $\beta$ is not more than 0.25.

21. A process for producing dialkanolamines according to claim 19, in which a part or all of the formed monoalkanolamine is recycled into the starting material system.

22. A process for producing dialkanolamines according to claim 21, in which the amount of the monoalkanolamine to be recycled into the starting material system is not more than $0.3R\beta^{0.5}$ to the amount of the total alkanolamines formed, when the mole number of ammonia per mole of the starting alkylene oxide is R.

23. A process for producing dialkanolamines according to claim 19, in which the catalyst has the outer surfaces of its primary particles which have been given a deactivating treatment.

24. A process for producing dialkanolamines according to claim 23, in which a part or all of the formed monoalkanolamine is recycled into the starting material system.

25. A process for producing dialkanolamines according to claim 24, in which the amount of the monoalkanolamine to be recycled into the starting material system is not more than $0.3R\beta^{0.5}$ to the amount of the total alkanolamines formed, when the mole number of ammonia per mole of the starting alkylene oxide is R.

26. A process for producing dialkanolamines according to claim 23, in which said reaction rate constant $\alpha$ is in the range of 0.10 to 0.30, and said reaction rate constant $\beta$ is not more than 0.25.

27. The process for producing dialkanolamines according to claim 26, in which a part or all of the formed monoalkanolamine is recycled into the starting material system.

28. A process for producing dialkanolamines according to claim 27, in which the amount of the monoalkanolamine to be recycled into the starting material system is not more than $0.3R\beta^{0.5}$ to the amount of the total alkanolamines formed, when the mole number of ammonia per mole of the starting alkylene oxide is R.

* * * * *